United States Patent [19]

Matschke

[11] Patent Number: 5,498,394

[45] Date of Patent: * Mar. 12, 1996

[54] APPARATUS AND METHOD FOR A BIO-CONDITIONING GERMICIDAL DRYER

[75] Inventor: Arthur L. Matschke, Bethel, Conn.

[73] Assignee: Molecucare, Inc., Southport, Conn.

[ * ] Notice: The portion of the term of this patent subsequent to Jun. 1, 2010, has been disclaimed.

[21] Appl. No.: 211,796

[22] PCT Filed: Oct. 16, 1992

[86] PCT No.: PCT/US92/09201

§ 371 Date: Jun. 15, 1994

§ 102(e) Date: Jun. 15, 1994

[87] PCT Pub. No.: WO93/08588

PCT Pub. Date: Apr. 29, 1993

[51] Int. Cl.⁶ .............................. A61L 2/10; F26B 21/06
[52] U.S. Cl. .................... 422/24; 250/455.11; 34/275; 34/549; 34/565; 34/572; 34/82; 392/380
[58] Field of Search ............... 422/24, 121; 250/455.11; 34/275, 524, 549, 565, 572, 82; 392/380

[56] References Cited

U.S. PATENT DOCUMENTS

| 2,814,081 | 11/1957 | Stevenson | 422/116 |
|---|---|---|---|
| 3,117,832 | 1/1964 | Thomas | 422/23 |
| 3,683,638 | 8/1972 | Devon | 62/264 |
| 3,877,437 | 4/1975 | Maitan et al. | 607/91 |
| 4,087,925 | 5/1978 | Bienek | 34/60 |
| 4,201,916 | 5/1980 | Ellner | 250/372 |
| 4,772,795 | 9/1988 | Sakurai et al. | 250/455.11 |
| 4,786,812 | 11/1988 | Humphreys | 250/455.11 |
| 4,877,964 | 10/1989 | Tanaka | 250/455.11 |
| 4,950,902 | 8/1990 | Ritter | 250/455.11 |
| 5,216,251 | 6/1993 | Matschke | 250/455.11 |
| 5,290,510 | 3/1994 | Lee | 422/122 X |

Primary Examiner—Robert J. Warden
Assistant Examiner—E. Leigh Dawson
Attorney, Agent, or Firm—Pennie & Edmonds

[57] ABSTRACT

A bioconditioning germicidal dryer for the hands and lower arms has two portals which allows the hands and forearms to be comfortably extended laterally into the chamber. The working chamber has a source of ultraviolet light with a spectral output weighted at a 253.7 nm. Air is introduced through one or more vents in a second heated chamber connected to said working chamber. Preheated air is then drawn past the ultraviolet light source, where it is germicidally cleansed, into the working chamber, and leaves the working chamber through the portals. Because of the combination of (a) ultraviolet light, (b) closed chamber environment, (c) warm air and (d) chamber geometry induced turbulent air flow patterns, the hands and arms are germicidally cleansed and gently dried without dehydration of the skin normally found in germicidal washing.

35 Claims, 8 Drawing Sheets

APPARATUS AND METHOD FOR A BIO-CONDITIONING GERMICIDAL DRYER

BACKGROUND OF THE INVENTION

Medical health care workers, such as physicians, nurses, dentists and paramedics, constantly come into contact with infectious micro-organisms (viruses, bacteria, and spores) or body fluids containing such micro organisms. For example, medical health care workers in hospitals are routinely exposed to extremely dangerous and persistent pathogens such as Hepatitis B, *Staphylococcus aureus, Escherichia coli*, Candida, Listeria, Tuberculosis and viruses causing human immunodeficiency (HIV). Many pathogens, including the above listed micro-organisms, are carrier transient between non-infected and infected persons. Many of such pathogens can be transmitted by simple contact, such as on the hands of medical personnel. Thus, the risk of transmission exists even when the medical health care workers contact arises from non-invasive procedures.

Medical health care workers are constantly required to exchange their time and service between patients. Due to comparatively recent changes in the medical environment affecting the presence of lethal pathogens such as the appearance of HIV, the routine of patient contact is increasingly risk-laden for both the medical health care worker and his patients. If the medical care worker's hands and forearms are not properly cleaned or covered, the worker can act as a transmitter of the disease between patients or become a receiver of the disease himself. The wearing of gloves and hand washing with germicidal agents are the only personal disciplines for protection against such transmissions.

Hand washing is a method of germicidal cleansing which attempts to reduce pathogens on the hand to insignificant levels by trying to either kill or remove a significant percentage of them. Gloves are a barrier protection between the wearer and the patient. The gloves become contaminated through use, including contact with any non-sterilized surface. Thus the process of removing and replacing gloves is itself a contaminative one for the hands and lower arms. Hands should never be gloved, ungloved or re-gloved without germicidal cleansing. Accordingly, today's routine medical procedure, particularly in hospitals, requires a very high incidence of health care worker hand washing. In a normal day, medical health care workers do such hand washing between twenty and a hundred times.

Since many lethal micro-organisms are difficult to remove or destroy, simple washing techniques are not foolproof. Protocols for washing are not always completely followed. Pathogens can and do survive hand washing. The frequency of contact and exposure in health care facilities increase the likelihood of contagion through such residual contamination.

In addition, frequent hand washing creates problems of failing skin integrity due to the skin's intolerance to repeated use of anti-microbial chemicals and detergent soaps. Such failing skin integrity seriously increases the risk of infection of the health care worker and transmittal by the health care worker of infection between patients. The use of emollients to protect skin integrity defeats the antimicrobial cleansing and acts to contaminate the medical care worker's hands.

Hand washing protocols can be routinely maintained within medical care facilities, where sinks and disinfectants are a few steps away. However, a different situation exists outside such facilities. In ambulances, in rescue and fire trucks, in field clinics, and in police emergency vehicles, there are no such facilities. Remaining germicidally clean by conventional hand washing techniques is extremely difficult, if not impossible, in such environments. However, it is in these very environments that there is a particularly high-risk of pathogen contact-exposure.

It has long been recognized that pathogens can be destroyed in the air, in water or on exposed surfaces if they are irradiated with ultraviolet light at the wavelength of 253.7 nanometers. However, use of such ultraviolet light for germicidal cleansing has been severely restricted. It has been used to treat air or water, which is circulated past an ultraviolet source in a cabinet or the like and then into the use environment. Similarly ultraviolet light has been used to sterilize small objects in a closed environment.

For example U.S. Pat. No. 4,786,812 to Wesley G. Humphreys issued on Nov. 22, 1988 discloses a light weight and portable germ killing machine which is used to purify air which is drawn past a series of ultraviolet lights at the appropriate wavelength. Similarly, U.S. Pat. No. 4,950,902 to Charles H. Ritter, issued on Aug. 21, 1990, U.S. Pat. No. 4,877,964 to Yoshio Tanaka, issued on Oct. 31, 1989, and U.S. Pat. No. 3,683,638 issued to George S. Devon on Aug. 15, 1972 all disclose chambers where ultraviolet light is used as a germicidal agent.

This prior art does not teach the use of an enclosed ultraviolet chamber in which gloved or ungloved hands and arms can be inserted for a combination of germicidally cleansing and warm air and ultraviolet drying of the hands and arms after scrubbing. Equally, none of the devices disclose a chamber constructed to diffuse the ultraviolet light energy throughout the chamber to ensure that there is complete exposure to ultraviolet light at a desired level on all exterior surfaces of the hands and arms so inserted.

SUMMARY OF THE INVENTION

A drying and germicidal cleansing machine is disclosed for use as part of an antimicrobial washing protocol which provides for continued germicidal (anti-microbial) cleansing of the hands and forearms during drying by means of ultraviolet light. When used in conjunction with medical hand washing protocols, it enhances the protocols in three respects.

First, the ultraviolet light itself is a powerful germicidal agent which acts to complete germicidal cleansing. The overall germicidal cleansing effect used in combination with conventional medical washing techniques exceeds that of such a washing technique in combination with conventional drying techniques. This result is from the even distribution of germicidal ultraviolet light over the hands and arms of the medical health care worker in combination with the use of non-contact drying by disinfected air.

The use of the present invention, even without scrubbing, can act as an effective germicidal cleansing method. In situations such as in emergency rescue vehicles, where hand washing protocols are not practical, the present invention, in combination with a protocol for the removal of opaque debris normally removed by washing, can produce acceptable germicidal cleansing.

Secondly, through use of turbulent warm air in an enclosed environment and the beneficial effects of low level ultraviolet light on the skin, the present invention acts to prevent skin problems normally developed with the constant use of medical hand washing procedures and thus to preserve the integrity of the skin itself. Avoided are the accumulative damaging effect of abrasive drying, contaminative hot air drying and fast drying which exceeds skin hydration tolerance.

Thirdly, the present invention produces a germicidal cleansing and drying method which does not require special training or excessive discipline in use. This simplicity of operation acts to correct insufficient or incorrect washing resulting from inexperience or undisciplined hand washing techniques.

The present invention can also be used for germicidal cleansing of medical tools and closed environments.

The invention consists of a chamber set at counter height, having two portals located at a distance apart to simultaneously allow the hands and forearms to be comfortably extended laterally through them. The chamber has a source of ultraviolet light having a spectral output weighted at a 253.7 nm. Ultraviolet light at this wavelength is germicidal but only penetrates slightly into the skin, confining its action to the skin surface layers. Ultraviolet light as this wavelength is not as invasive as exposure to sun light with its broad spectrum of ultraviolet wavelengths. This, in combination with the uniform low levels of energy on any surface in the working chamber of the present invention, assures germicidal action without harm to the skin.

The interior geometry of the present invention is such as to uniformly distribute the rays of ultraviolet light throughout the working chamber. The working chamber is a closed reflective chamber with all ultraviolet light entering through a diffuser plate forming the bottom or floor of the working chamber. This corresponds to the distribution pattern of ultraviolet light entering a closed reflective chamber through a single aperture. As more fully described hereinafter, the chamber consists of an upper toroidal section, a central cylindrical section and a lower toroidal section. The diffuser is located in the lower toroidal section. The diffuser is transparent to ultraviolet light weighted at 253.7 nm. The ultraviolet light source is positioned under the diffuser in a second chamber in the lower toroidal section below the working chamber. Two portals in the upper toroidal section allow for insertion of the hands and arms into the chamber. Light emanating from the diffuser is reflected by the geometry of the working zone chamber to provide ultraviolet light at a uniform intensity. Since the chamber distributes the ultraviolet light source evenly throughout the working chamber, the inserted hands and forearms receive ultraviolet light over their entire surface. In the present invention, the ultraviolet radiation level is uniform throughout the working chamber at approximately 3.0 joules/m$^2$. A second ultraviolet light source may also be provided in the upper section of the working chamber to enhance the cleansing action cycle.

Air is introduced through one or more air inlets or vents in the second chamber. Preferably the entering air is filtered. Before entering the working chamber the air is heated by a conventional electrical heater and passes by the ultraviolet source to be germicidally cleansed. The heater also acts to heat the entire second chamber and the walls forming the chamber by convection and conduction. This aids in the maintenance of a minimum temperature gradient across the working chamber. A fan draws the heated air into the working chamber past the ultraviolet source, and in combination with the working chamber geometry, produces a turbulent stream of dry warm air which circulates throughout the working chamber and in particular, over the user's hands and forearms. As a result, "hot" and "cold" spots are avoided, i.e., there is a minimal temperature gradient within the chamber and the moisture evaporation rate over the skin surface is relatively low to prevent excessive drying. The second chamber can also contain a third ultraviolet source for irradiating the surfaces of the structures contained in the second chamber.

Due to the construction of the working chamber and the seal between the working chamber and the second chamber, a positive pressure is maintained in the working chamber. Air enters the second chamber, is drawn past the ultraviolet light source and leaves the working chamber through the portals. When hands and lower arms are inside the working chamber, the hands are only in contact with air which has been germicidally cleansed by direct exposure to the ultraviolet source before entry into the chamber. Because of the combination of (a) the closed chamber environment, (b) the use of warm air, rather than hot air and (c) the chamber geometry induced turbulent air flow patterns, the hands and arms are gently dried without dehydration of the skin normally found in the use of air dryers. This effect is enhanced by the presence of the ultraviolet light which also acts to remove water from the hands without inducing excess dryness.

In operation, the chamber has a photo-electric switch which detects the insertion of the hands into the chamber to start the cleansing and drying cycle. The ultraviolet light is turned on, the fan and heat commences operation. Alternatively, the heater and fan may be operated continuously to assure uniform conditions in the working chamber. A timer limits the length of ultraviolet cycle. In most uses, the preset cycle is 15 seconds. This kills most common lethal microorganisms. Under special circumstances the timer can be reset or the cycle repeated when it is judged that additional exposure is required.

The automatic cycling avoids the need for physical contact of the user's hands and arms with the chamber and recontamination arising from such contact. A second circuit prevents restart of a cycle during a cycle. A circuit is provided to insure a delay between cycles. Since all cycles may be pre-set, use requires minimal operator skill and time.

The use of this chamber creates a very efficient germicidal procedure for drying hands as part of a medical wash which reduces the required skill and discipline for achieving germicidally cleansed hands. The present invention's simplicity of the operation itself ensures its use since it is easily incorporated into the user's working procedures. The simplicity of operation provides a germicidal method which can be used by law enforcement and emergency care givers or other persons having risk of exposure in a non-hospital or non-medical office environment where washing is not possible.

The present invention physiologically enhances the hand washing regimen by providing a moderate skin surface evaporation rate using an efficient combination of warm turbulent germicidal cleaned air and ultraviolet radiation. Not only does this environment produce a pleasant sensation during drying, the user maintains higher skin moisture levels and skin integrity, not normally associated with constant use of anti-microbial hand washing procedures.

Because of its design, the anti-microbial and drying effect of the present invention reaches to the upper forearm area. Because of the difficulty in washing and drying the upper arm areas, absent extremely careful washing techniques, contaminated droplets of water may remain. When the arms are normal positioned after scrubbing such droplets may recontaminate the hands. Thus under present scrubbing techniques, surgeons hold their hands vertically upward after scrubbing to avoid contamination prior to donning the gloves. The present invention permit a germicidal cleansing and drying while hands are held in a downward position. The droplets are eliminated before substantial downward migration and the affected area is germicidal cleansed.

These and other objects and many attendant advantages of the present invention will be readily appreciated as the same become better understood by reference to the following detail description when considered in connection with the accompanied drawings.

DETAILED DESCRIPTION OF THE PREFERRED EMBODIMENTS

Figure 1:
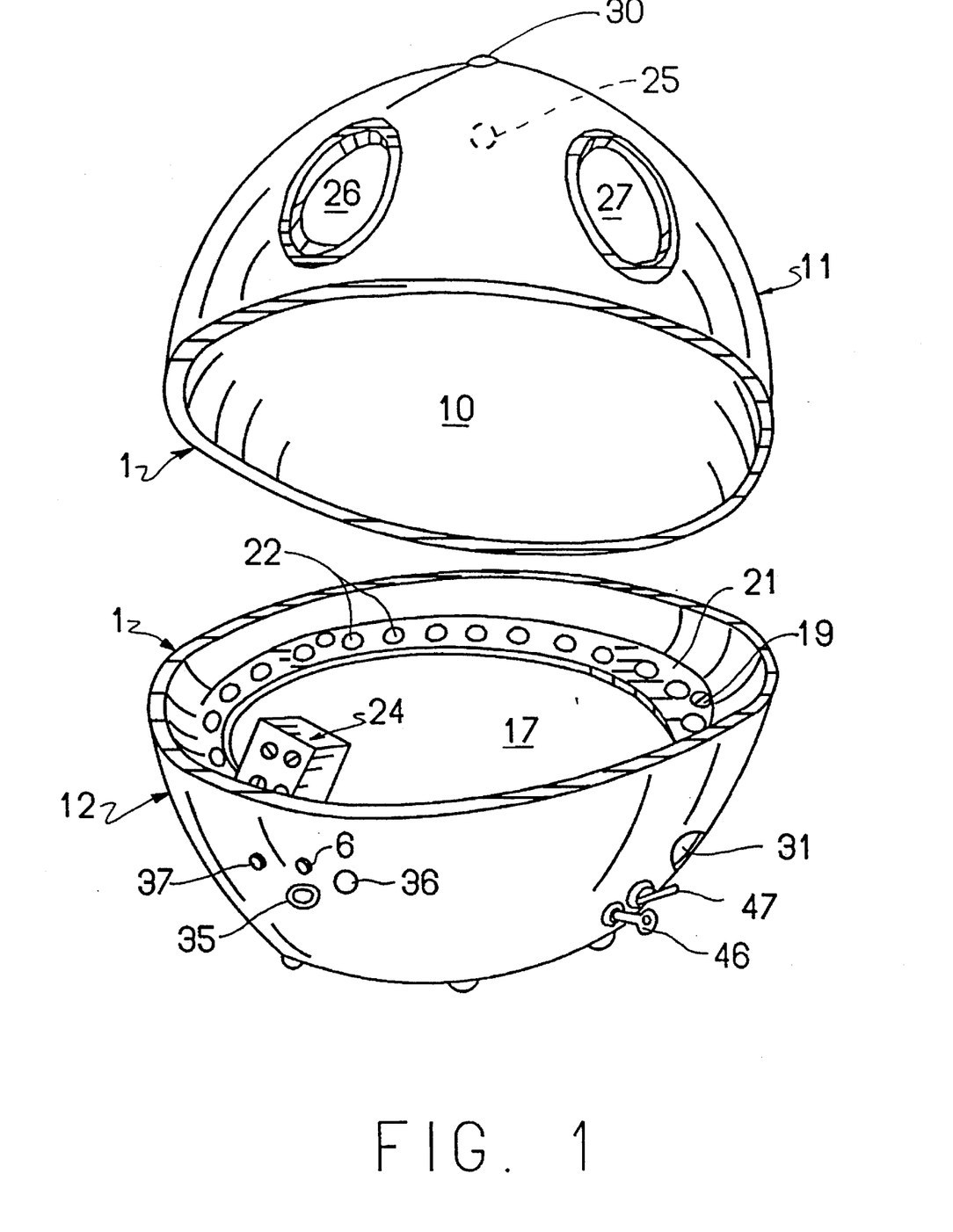
FIG. 1 is a perspective view of the germicidal cleansing and drying apparatus of the present invention with the upper portion of the working chamber being lifted off and above the lower portion of the working chamber and slightly rotated in relation thereto and without the plastic collars surrounding the portals.

As seen in FIG. 1, the germicidal cleansing and drying apparatus of the present invention 1 is formed by an upper member 11 and a lower member 12 which, together with the diffuser 17 mounted in the lower member 12, define the working chamber 10 and a second chamber 2. All interior surfaces of the chambers are made from spun aluminum with a non-polished finish. The diffuser 17 is mounted on the reflector 13. Reflector 13 is attached to lower member 12. The reflector 13 faces the interior of the working chamber 10. The center of the reflector 13 has a central concave surface 15 with an opening 16 at its center.

Mounted in and on top of the reflector 13 is ultraviolet light source 14. The ultraviolet light source 14 can be an industrial rated germicidal bulb, with emission in the far ultraviolet wavelength, weighted at 253.7 nm. This wavelength has been found to be particularly useful in the destruction of pathogenic microorganisms. Ultraviolet light at this wavelength penetrates only the surface cells of the skin, allowing germicidal cleansing of only the superficial skin layers. The intensity of the bulb is selected to produce the desired level of ultraviolet radiation in the chamber 10, the intensity or irradiance of the ultraviolet light in the working chamber 10 determines the cycle time, and thus exposure time of hand and arms in the chamber. As shown, the ultraviolet light source 14 is straight tube. Alternately, a bulb of a circular or other configurations may be used to achieve identical or near identical performance. Mounted above ultraviolet light source 14 is an ultraviolet diffuser 17. The diffuser 17 may be formed from any material which transmits ultraviolet light at 253.7 nm. Plastic or quartz combinations which are transparent to desired wavelengths are all suitable. The diffuser 17 perimeter has been treated by grinding, sand-blasting or similar abrasion, to create diffusion scattering in the 253.7 nm wave length region.

Figure 3:
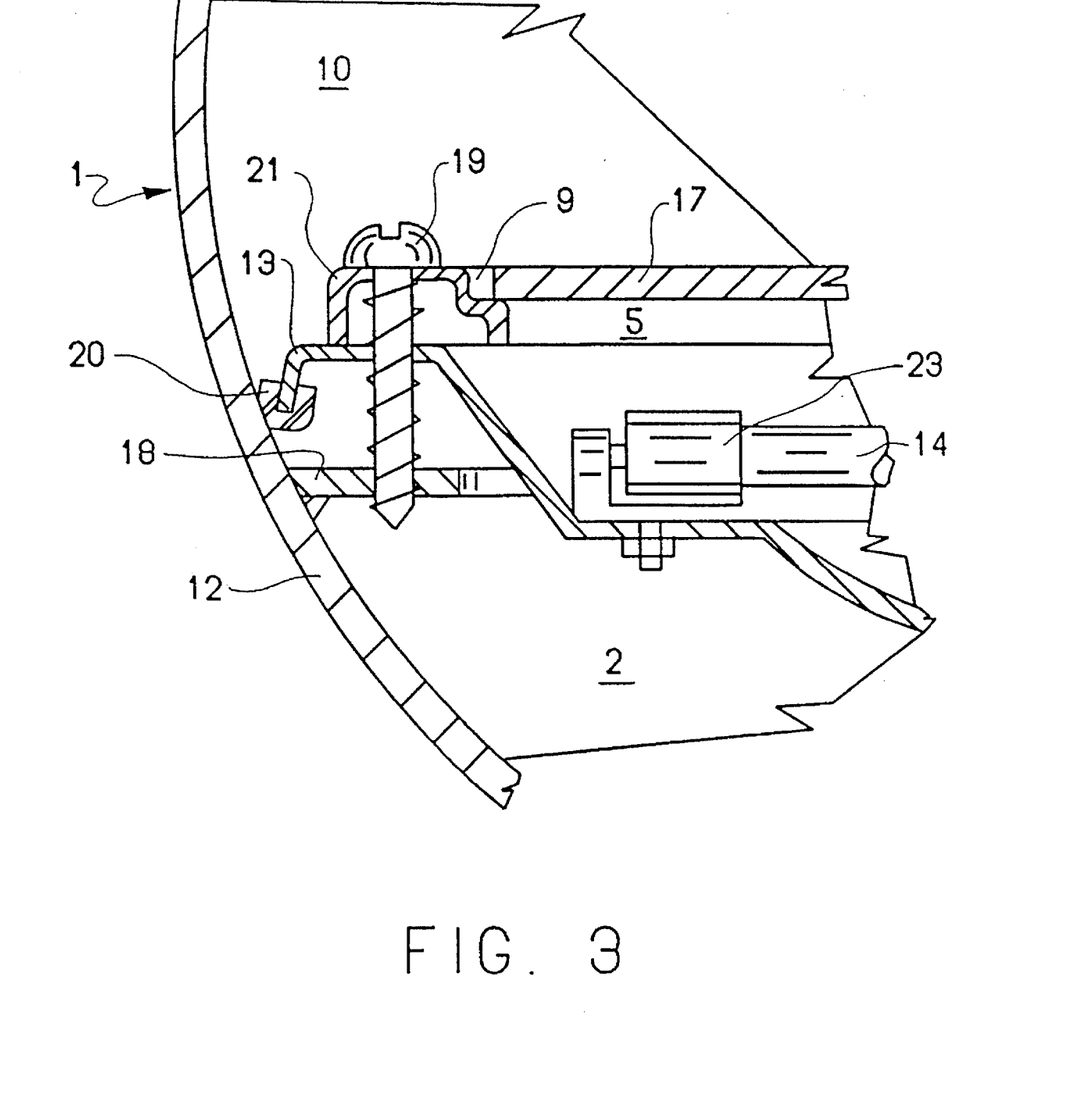
FIG. 3 is a partially cut away front view of a portion of the working and second chambers showing the details of the mounting of the ultraviolet light source and the ultraviolet light diffuser.

The method of mounting diffuser 17 to reflector 13 to lower member 12 is most clearly seen in FIG. 3. Mounted on the side of lower member 12 by welding or the like is a ledge 18 which has three holes for the receiving screws 19 mounted equidistantly around its surface. Reflector 13 is mounted inside the central opening of ledge 18. It is held in place against the wall of lower member 12 by screws 19. A sealing element such as a neoprene grommet 20 is positioned around the edge of reflector 13. Grommet 20 seals the working chamber 10 to prevent recirculation of air in the chamber and to maintain positive pressure in the working chamber 10 itself. Diffuser positioning ring 21 holds diffuser 17 in place. It is mounted on top of reflective 13 by screws 19. Ring 21 has a series of apertures or holes 22 around its upper surface to allow circulation of air through the reflector 13 into the working chamber 10. The diffuser 17 mounted on ring 21 is held in place by an ultraviolet resistant cement 9 such as a silicone cement. The ultraviolet light 14 is mounted on reflector 13 by a conventional mounting assembly 23.

The diffuser 17 and ring 21 form a cover over reflector 13, providing an enclosure 5 about the ultraviolet light source 14. Alternatively, diffuser 17 and ring 21 may be combined as one piece and made of an ultraviolet transmitting material. Also mounted on the upper outer surface of reflector 13 is a photo-electric sensor and momentary switch 24 which, in conjunction with reflector 25 mounted on upper member 11 is used to automatically control the operating cycle of the working chamber 10. Light travels back and forth between sensor and momentary switch 24 and reflector 25 in light path 8. Interruption of the light by positioning of an opaque object in the light path 8 closes the momentary switch 24.

There are two openings or portals 26 and 27 in the working chamber 10 to allow insertion of the hands and arms into the chamber. The portals 26 and 27 have mounted on them plastic collars 28 and 29 of low reflective material to prevent eye contact with the interior of the working chamber 10 during an ultraviolet cycle. When arms are inserted in portals 26 and 27, the plastic collars 28 and 27 also act to prevent substantial leakage of ultraviolet light outside the working chamber 10. At the top of upper chamber 11 is a ultraviolet opaque window or lens 30 to allow viewing of the interior of the working chamber 10.

Figure 2:
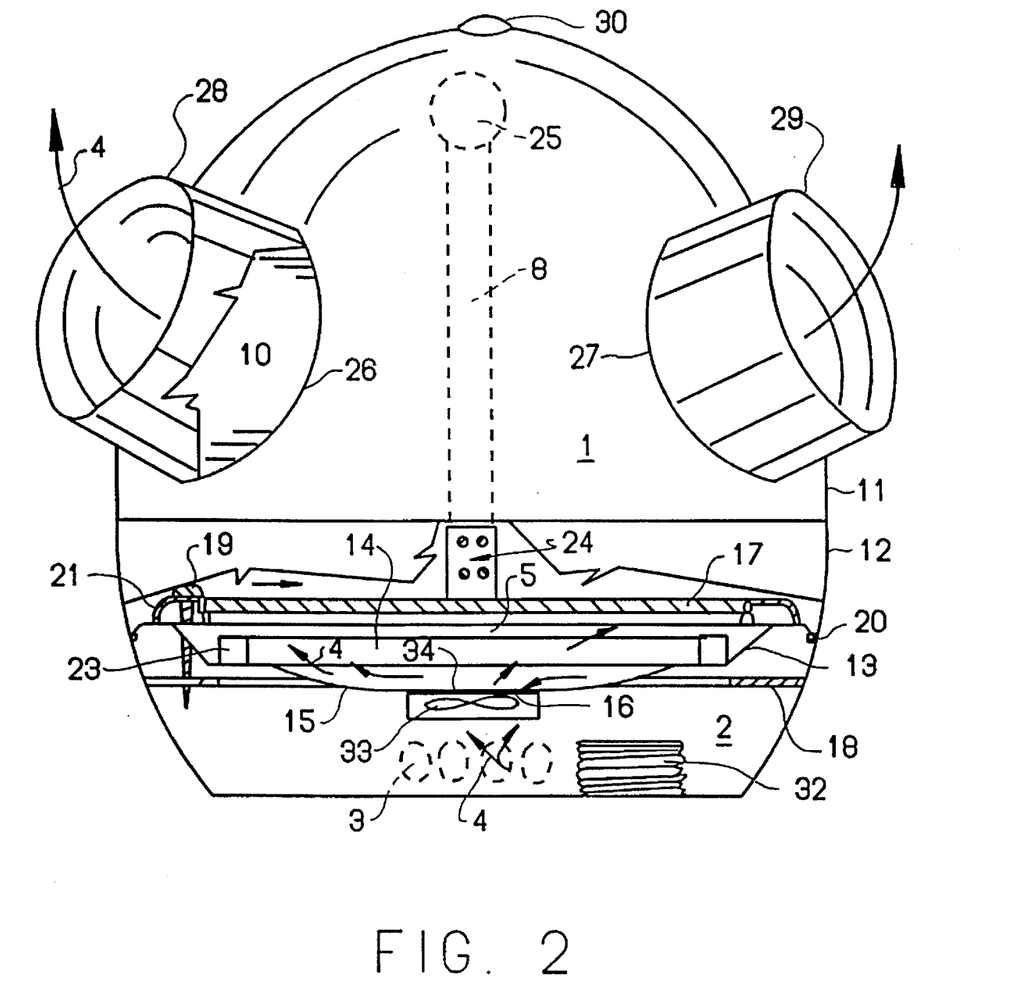
FIG. 2 is a partially cut away front elevational view of the present invention with arrows representing the air flow patterns in the lower and working chambers and through the portals and with the photo-electric sensor target and path of the photo-electric sensor beam and the working chamber shown in the dotted lines.

In the embodiment of FIGS. 1–2, the second chamber 2 has holes 31 for the entry of fresh air mounted below and to one edge of reflector 13. A filter 3 may be mounted over the air holes. Adjacent air entry holes 31 is a heater coil 32. Mounted below the reflector 13 at the reflector's 13 central opening 16 is a fan 33 for moving air heated by heater 31 into working chamber 10. It has a filter 34. The warm air passes through the reflector 13 past the ultraviolet light source 14 where it is germicidally cleansed and further heated. It then passes through holes 22 in the ring 21. The flow of air from holes 31, past the ultraviolet source 14, and through the working chamber 10 is shown by arrows 4 in FIG. 2. Seal 20 helps maintain this flow pattern and assure that air is not circulated from the second chamber 2 without passing the ultraviolet source 14. A positive pressure is maintained in the portals 26 and 27 assuring that ambient unsterilized air does not enter the working chamber 10 during an ultraviolet light cleansing cycle. This air path provides, warm, turbulent cleansed air under positive pressure in the working chamber 10.

On the exterior of the chamber are four indicator lights 35, 36, 37 and 6 which when lit indicate, respectively, power on, heat on, cycle ready, and cycle on as will be more fully explained below.

The geometry of the working chamber 10 is such as to promote the distribution of the ultraviolet light passing through the diffuser 17 evenly throughout the working chamber 10 and to assure turbulent movement of the heated air throughout the working chamber 10. The dimensions of the working chamber 10 is defined by the normal anatomy of hands and arms. It is desired to meet these geometric needs while simultaneously assuring an elongated working zone for the ultraviolet light which would extend throughout the working chamber 10 and to cover all areas of the arm and hands of the user while assuring the proper flow of air throughout the chamber.

Figure 4:
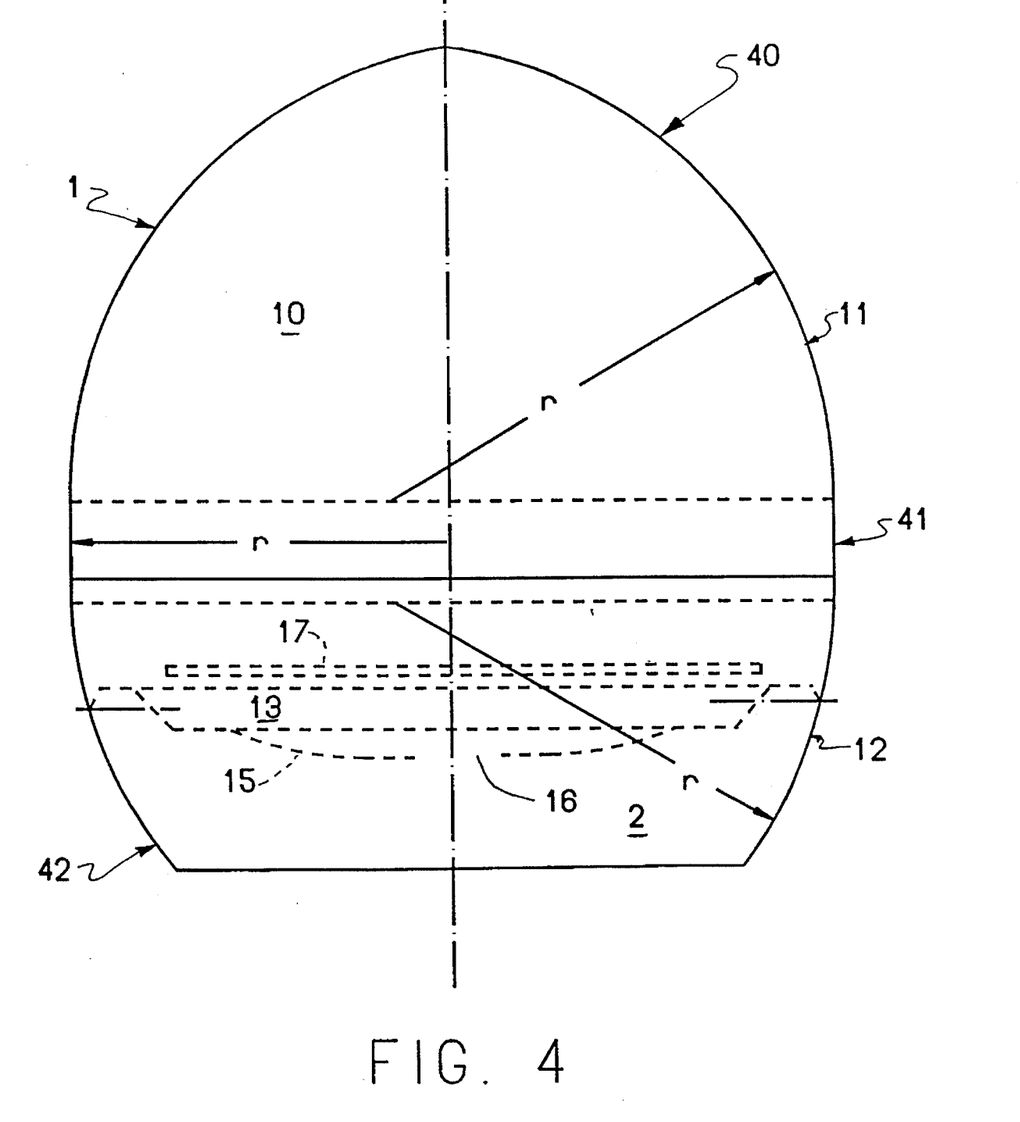
FIG. 4 is a diagrammatic representation of the cross-sectional configuration of the working and second chamber of the present invention.
Figure 5:
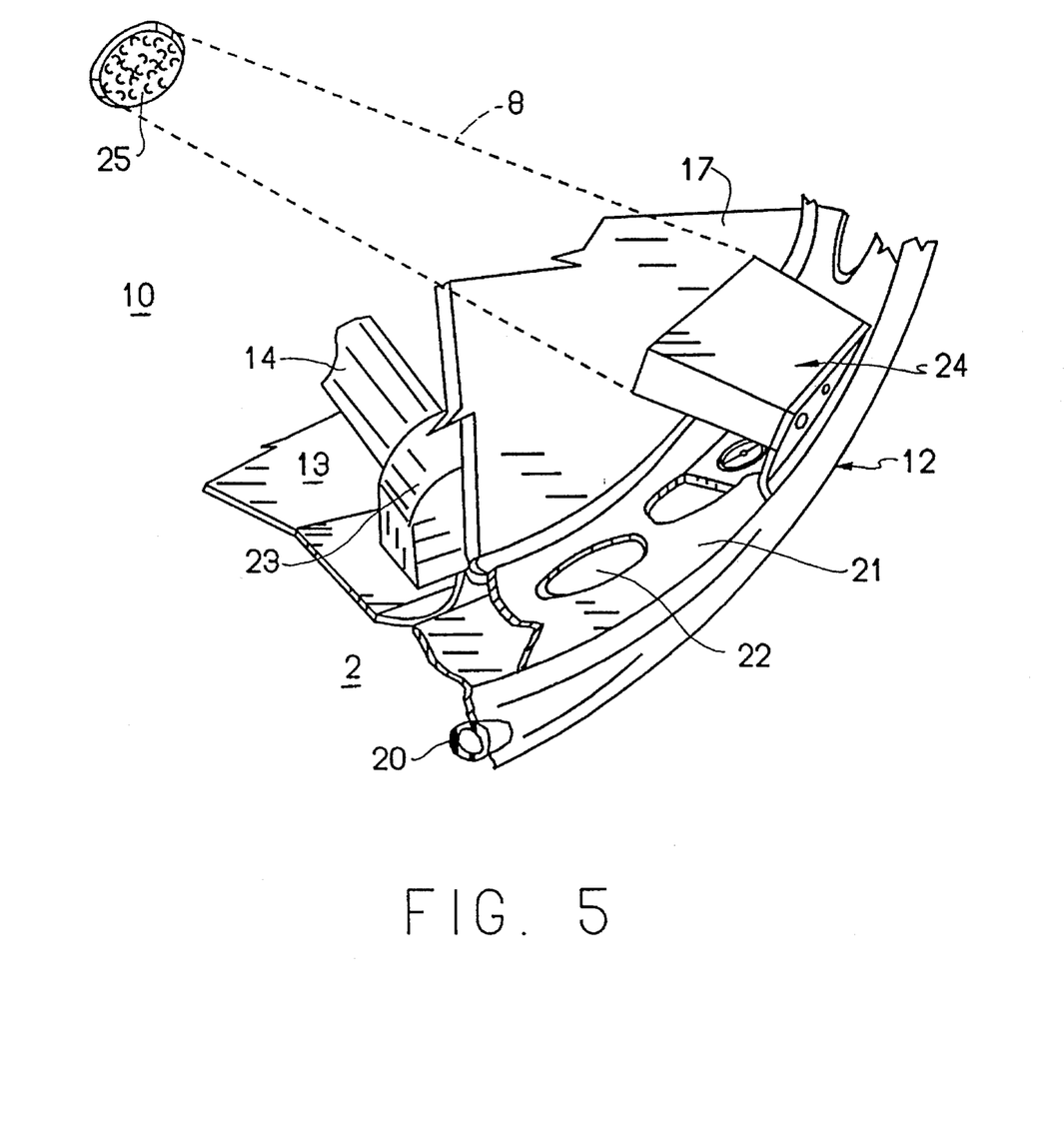
FIG. 5 is a fragmentary, partially cut away perspective view of a portion of the bottom of the working chamber with a photo-electric sensing system mounted in said working chamber and with the light path between the sensor and the target of the sensing system shown by dotted lines.

As seen most clearly in FIG. 4, the interior of the working chamber 10 of the preferred embodiment of the present invention is divided into annular rings with different configurations to facilitate reflection of the ultraviolet throughout the chamber. It was found that the configuration of the upper portion 40 of the working chamber 10 should be that of a toroid, having a radius of ten inches and its center of rotation being a three inch diameter circle around the central axis of the working chamber 10. The central segment 41 of the chamber 10 is in the form of a cylinder having a radius of eight and one half inches. The center of rotation of the toroid of the upper portion 40 of working chamber 10 is in the same plane as the top of the central segment 41. Accordingly, the center of cylindrical section 41 should theoretically meet perfectly with the toroidal section 40. However, due to limitations of metal construction and normal tolerances, it may be necessary to have a blend zone between these two segments. Lower section 42 is also formed of a toroid having a radius of ten inches and having a center of curvature which rotates in a circle having a diameter of three inches. It meets with central cylindrical portion 41 at a plane through which its center of curvature passes. In actuality there may also be a blend zone. In the preferred embodiment, the cylindrical central portion 41 extends from three to five inches. The bottom of the working chamber 10 is formed by the diffuser 17 mounted on the reflector 13. In the preferred embodiment, the second chamber is formed in a continuation of toroid forming the lower section 42.

Figure 6:
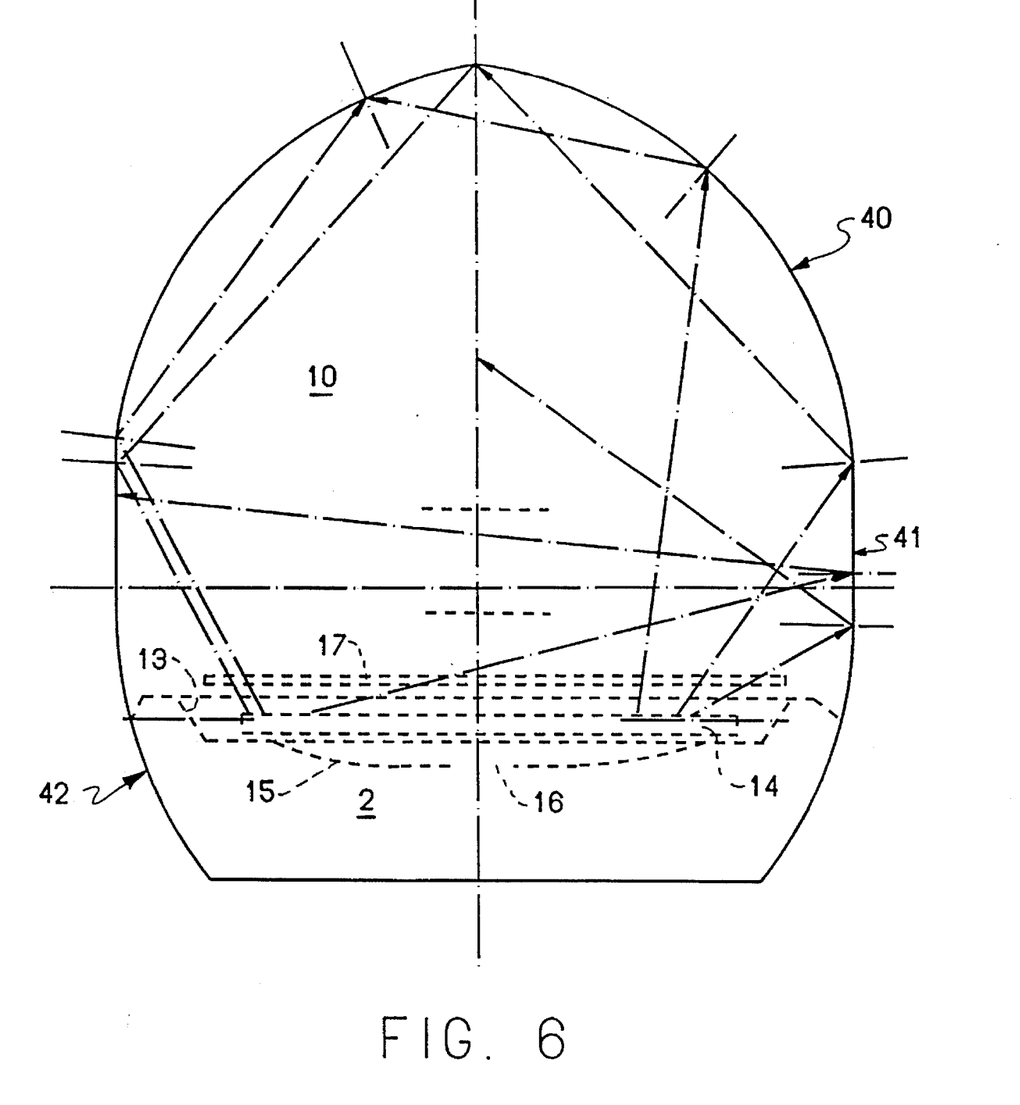
FIG. 6 is a schematic diagram of the chamber showing typical optical reflectance paths of rays from the ultraviolet light source in the working chamber.

This configuration allows a near uniform dispersion and reflection of light throughout the entire working chamber 10. Rays from any point in the diffuser 17 are reflected from the walls of the working chamber 10. The interior surfaces of the working chamber 10 are optically designed to evenly disperse ultraviolet light through the chamber. Examples of reflective patterns of selected rays are shown in FIG. 6. A light produced by an ultraviolet source 14 either directly enters the chamber through diffuser 17 or is reflected off reflector 13 and then through the diffuser 17. All ultraviolet light incident upon the walls of the working chamber 10, except for a minimal absorption, is directed towards the center axis of the chamber.

The shape of working chamber 10 does not concentrate the radiation in one specific position as would for example a sphere, but rather disperses the light throughout the working chamber 10. While specific dimensions which conform to the average human anatomy have been used to determine the size and shape of the working chamber 10, other dimensions may be made to meet special needs. Examples are working chambers 10 used in germicidally cleansing and drying areas of body parts in burn cases, such as arms, legs, or even entire torsos. Equally smaller units for germicidally cleansing of children and infants may be provided.

Figure 7:
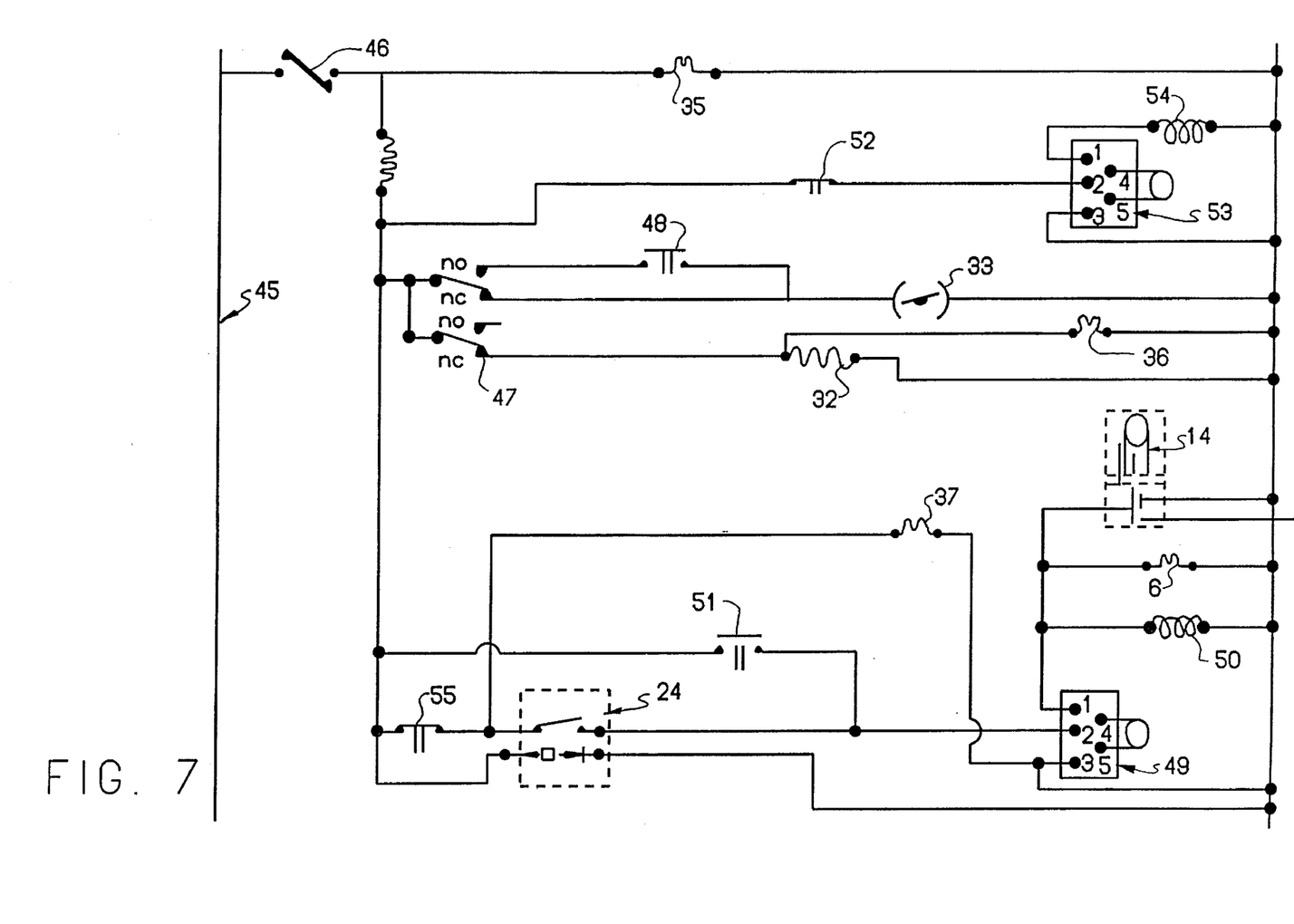
FIG. 7 is a schematic diagram of the electrical system of the present invention.

FIG. 7 shows the electrical configuration of the operating system of the present invention. Situated between the power source 45 and the electronic switching system of the present invention is master switch 46. When the switch 46 is in the "on" position, light 35 on the front of the apparatus 1 is lit, indicating that the power is on. Switch 47 turns the heater 32 on, simultaneously lighting the "heat on" light 36 on the front panel. The switch 47 also simultaneously turns on the fan 33. When switch 47 is in the "off" position, it closes a circuit to the fan 33 which is controlled by a relay contact 48 which is activated whenever the ultraviolet light 14 is on through relay coil 50. Thus fan 33 either operates when the heater 32 is on, when the ultraviolet light 14 is on, or when both are on.

Operation of the ultraviolet light 14 is initiated when photo-electric momentary switch 24 indicates that there are objects such as hands and arms in the working chamber 10, closing the relay coil 50, and allowing electricity to pass through a timer 49. Timer 49 supplies electricity to the ultraviolet source 14 and "cycle on" light 6 for the duration of its cycle because relay coil 50 holds relay contact 51 closed during the cycle. Timer relay 49 opens at the end of its cycle which releases relay coil 50 which opens relay contact 51 cutting off electricity to the timer 49. Relay coil 50 also controls relay contact 52 which is intermediate between the master switch 46 and a second timer 53. Timer 53 controls the length of intervals between which the cycle can be activated. Relay contact 52 is normally in a closed position.

Upon activation of timer relay 49, relay coil 50 opens relay contact 52. Upon the initial closing of switch 46 or the termination of the cycle by timer 49, which releases relay coil 50, current is supplied to timer 53 which starts its cycle. This operates relay coil 54 which opens relay contact 55 thereby disabling timer relay 49 for the duration of the cycle of timer 53. At the end of its cycle, timer 53 releases relay coil 54 again closing relay contact 55 and allowing timer 49 to be in a ready position. This in turn also closes a circuit with a pilot light 37 indicating that timer 49 is in a ready state.

In use, the apparatus is turned on by turning switch 46 to the "on" position. If it is desired, the fan and heater can be continuously operated even when a cycle is not in progress. The heater and fan can then be turned on by heat switch 47. This improves drying by keeping the ambient temperature of the working chamber 10 at a uniform level. Alternatively the heater and fan can be operated only during the operational cycle.

After conducting a normal medical wash which both cleans and removes particles and debris, the hands and arms are inserted into portals 26 and 27. This in turn initiates a cycle wherein the ultraviolet light 14 is lit for a standard cycle period. As discussed above, the ultraviolet light is uniformly reflected throughout the working chamber 10 so that surfaces of the user's hand and arms will be evenly irradiated. In an environment having ultraviolet light weighed at 253.7 nm at a radiation level of approximate 3.0 joules per square meter, it has been found that most pathogens are killed within a few seconds. Additional time is allocated to allow movement of the hands throughout the chamber to assure consistent exposure of the hand to the ultraviolet light and warm air, as well as to allow drying action. Accordingly the cycle time is generally set between 15 and 18 seconds. This is sufficient time to both dry the hands and continue the germicidal action. If the hands are not dried within the normal cycle range, continued drying can be conducted without exposure to ultraviolet light by positioning the hands outside the electrical eye's path with the continuous heat switch 47 in the "on" position.

It has been found that the optimum drying and sterilization effect comes from following a protocol within the chamber of rolling in the hands slowly, finger tips extended and spread, alternately bending fingers and touching fingernail tips to diffuser 17 with the palm downward. This assures even exposure to the ultraviolet light on all surfaces of the hand.

At the end of the cycle, the hands are removed. Timer 53 assures that the cycle cannot be initiated again if the hands remain in the chamber. In certain cases the ultraviolet light, without use of the heater, is sufficient to perform drying at a slower rate. Such use may be preferable in cases, such as in burn cases. There are other cases,, such as pure germicidal cleansing use, where the heater may be turned off.

Figure 8:
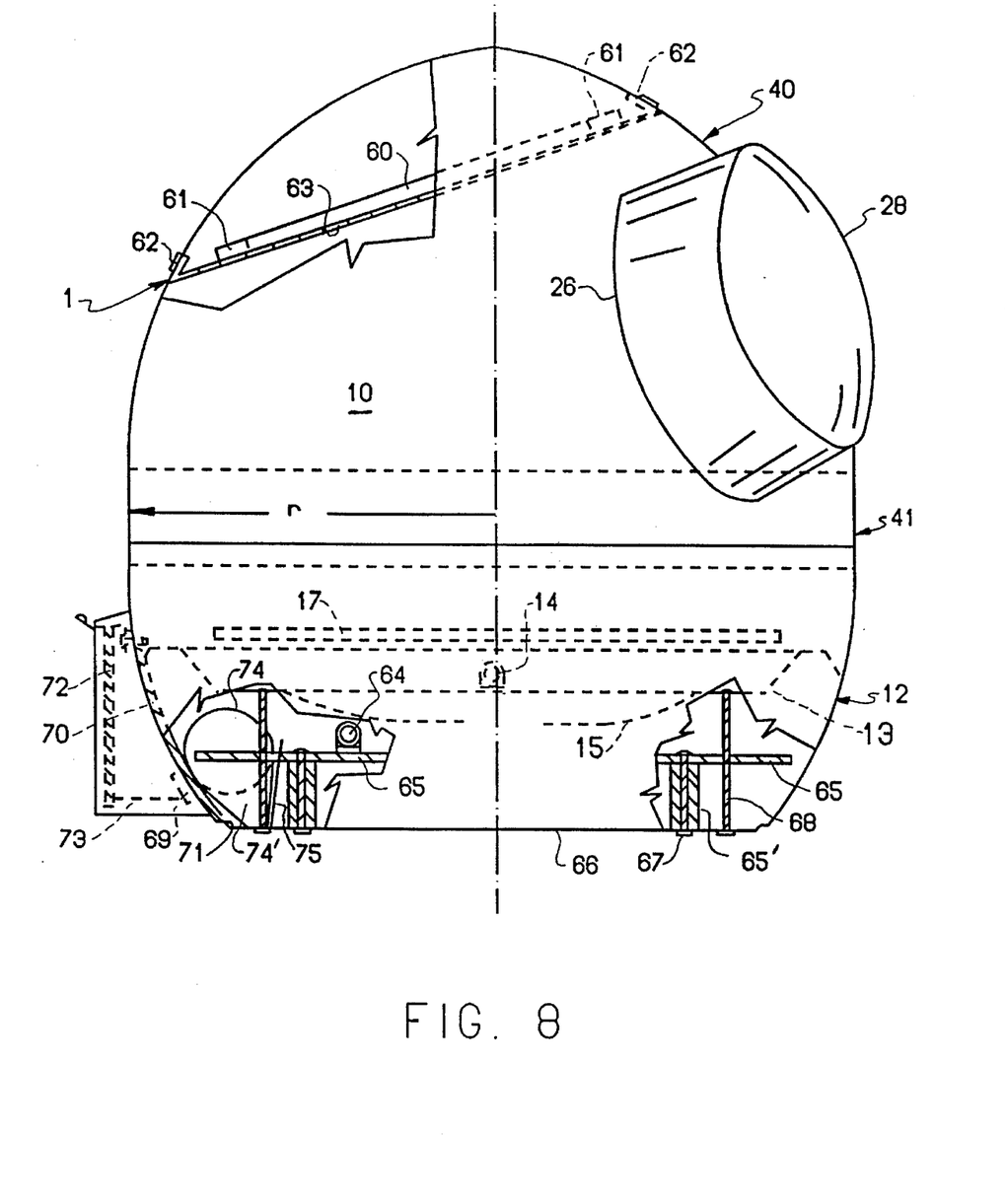
FIG. 8 is a partially cut away side elevational view of a modified embodiment of the present invention.

FIG. 8 shows a modified embodiment of the invention. In this embodiment many parts are the same as the embodiment of FIGS. 1–6. Accordingly, the same reference numbers for these parts are used in FIG. 8. The embodiment of FIG. 8 differs from the earlier embodiment basically with respect to the number and positioning of additional ultraviolet light sources and the construction of the lower housing member and internal structure.

As shown in FIG. 8, a second ultraviolet light source 60 is provided in the working chamber 10. This light source is positioned in the upper portion of the working chamber above the portals 26 and 27. It has the same wavelength characteristics as the first source 14. Also, in construction, the second light source has a straight configuration like the construction of the first light source 14. This configuration can however be circular or another shape more complementary to the internal wall surface of the working chamber. With the straight configuration, the second light source 60 is positioned in a plane extending between the portals 26 and 27. This second light source extends upwardly from the rear of the chamber to the forward portion of the chamber between the portals and is disposed at right angles to the first ultraviolet light source 14. The second ultraviolet light source is connected at its ends into suitable lamp sockets 61, which are, in turn, connected by brackets 62 to the wall of the working chamber.

A light shield member 63 is also connected to the bracket 62. This shield is positioned below the second light source 60 for protecting it against contact. The light shield member is perforated to transmit ultraviolet rays unaltered by attenuation through the shield. The shield material is transparent to ultraviolet light at 253.7 mn. A suitable shield is sold under the trademark Acrylic OP-4, by Cyro Industries of Mount Arlington, N.J.

The second ultraviolet light source 60 heightens the ultraviolet intensity from above the working chamber. The net radiation constant is unchanged in the working chamber as the values are directional. However, the second light source enhances the irradiation of the second chamber and permits shorter cycle times.

The second ultraviolet light source is connected electrically into the electrical system of the apparatus in the same way as the first light source 14. Both light sources cycle together as previously described.

In the embodiment shown in FIG. 8, a third ultraviolet light source 64 is provided. This light source is located in the second chamber, below the reflector. This third light source emits ultraviolet light at the same wavelength as the first and second light sources 14 and 60. The third light source is mounted on a support 65 having suitable legs 65' for positioning the support in a location spaced between the reflector 13 and the bottom wall 66 of the second chamber. The support is made of the same ultraviolet transparent material as the shield 63 in the upper portion of the working chamber 10. Therefore, the ultraviolet light source 64 irradiates the entire area of the second chamber between the reflector 13 and the bottom wall 66 and thereby minimizes the opportunity for pathogen build-up in this zone and on any of the surfaces of the structure contained in this zone.

The support 65 is removably secured in the bottom of the second chamber by bolts 67 extending through the bottom wall 66 of the chamber and the legs 65'. The support 65 together with the structure mounted on it, including the third light source 64, can therefore be preassembled and secured to the second chamber as a unit for removal and repair if necessary. Similarly, bolts 68 secure the reflector unit to the second chamber. These bolts also extend through the bottom wall of the chamber for ready access. In this way, both the reflector 13 and the diffuser 17 can be preassembled as a unit and installed for removal when repair is necessary. Also, with the three point securing of the reflector unit, the seating of the grommet 20 of the reflector along the chamber wall can be adjusted to assure proper sealing about its entire circumference.

In the embodiment disclosed in FIG. 8, a pair of air filters is provided for filtering the air entering the second chamber through the air inlet opening 69. The first of these filters 70 is mounted internally of the second chamber on the internal side wall surface 71. The second filter 72 is mounted externally of the wall surface. It also covers the air inlet opening 69, but is mounted for ready replacement by the user of the apparatus. Both filters are sealed around their peripheries to the wall structure to prevent unfiltered air from entering the second chamber and filter the incoming air to one micron. A preferred filter is one sold by the 3M Corporation under the trademark Filtrete. The removable filter 72 is mounted in bracket structure 73 secured to the external wall of the second chamber.

Disposed immediately inwardly of the air inlet opening 69 is a cylindrical heater assembly 74. This assembly is mounted by brackets 74' to the bottom wall 66 of the second chamber. A shield 75 extending from the bottom wall 66 to slightly above the support 65 protects the support against the heat generated by the heater.

With the embodiment of FIG. 8, the cleansing action in the working chamber is enhanced in that a shorter cycle is required to effect proper cleansing. Also, the inclusion of the ultraviolet light source in the bottom of the second chamber further treats incoming air and the surfaces in this chamber to effectively cleanse them. The filters further cleanse the air entering the second chamber.

While the invention has been described as having certain preferred designs, it is understood that it is capable of further modification, uses and/or adaptations following in general the principal of the invention and including such departures from the present disclosure as come within known or customary practice in the art to which the invention pertains.

I claim

1. An ultraviolet germicidal chamber comprising:
   a housing having an internal wall defining a working chamber and a second chamber;
   at least one portal in said housing communicating directly between said working chamber and outside of said housing;
   a first ultraviolet light source positioned in the second chamber; and
   an ultraviolet light diffuser positioned between the ultraviolet light source and the working chamber.

2. An apparatus according to claim 1, further comprising:
   a reflector positioned on the other side of the ultraviolet light source from the diffuser, said reflector having a reflector opening therein;
   an air inlet opening in the wall of said second chamber; and
   fan means located between said air inlet opening and said reflector opening to draw air from said second chamber through said reflector opening, past the ultraviolet light source and into the working chamber.

3. An apparatus according to claim 2 further comprising:
   a first filter covering said air inlet opening for filtering incoming air, said first filter being mounted internally of said housing; and
   a second filter covering said air inlet opening for filtering incoming air, said second filter being removably mounted externally of said housing for periodic replacement.

4. An apparatus according to claim 2 wherein:
   the fan means is positioned adjacent the reflector opening to direct air through said second chamber, past the ultraviolet light source and into the working chamber such that within the working chamber there is a flow of germicidally cleansed, turbulent air throughout with a flow of germicidally cleansed, turbulent air throughout with the avoidance of severe temperature or evaporation gradients.

5. An apparatus according to claim 2, further comprising:
   a heater positioned in said second chamber to heat the air to be drawn past the ultraviolet light source and into the working chamber.

6. An apparatus according to claim 2, wherein:
   said diffuser is sized and positioned relative to said light source, reflector and working chamber whereby light produced by said light source on any point on the diffuser and passing directly through said diffuser or passing indirectly through the diffuser by being reflected off of said reflector is reflected off the wall of the working chamber.

7. An apparatus according to claim 6 wherein:
   the working chamber has an interior wall surface shaped to direct all ultraviolet light incident upon the walls of the working chamber uniformly throughout the chamber.

8. An apparatus according to claim 2, further comprising:
   control means for controlling said ultraviolet light source such that when a part of the human anatomy is positioned through said portal into the working chamber, the ultraviolet light source is activated for a set period of time.

9. An apparatus according to claim 8 wherein:
   upon activation of the ultraviolet light source, said heater and fan means are also activated.

10. An apparatus according to claim 2, further comprising:
    positioning means for positioning the diffuser adjacent the ultraviolet light source, said positioning means engaging the diffuser and the reflector to form in conjunction with said reflector and said diffuser an enclosure about the ultraviolet light source.

11. An apparatus according to claim 10 wherein:
    said positioning means includes spaced apertures located in surrounding relation with respect to said diffuser for permitting flow of said air into said working chamber after passing the ultraviolet light source.

12. An apparatus according to claim 11 further comprising:
    sealing means for sealing the working chamber from the second chamber along said internal wall to prevent recirculation of air along said wall from the working chamber to the second chamber.

13. An apparatus according to claim 12, wherein:
    the reflector is circular in shape and has a downwardly curved center bottom portion surrounded by a laterally extending flat section which is, in turn, surrounded by an upwardly and radially outwardly slanted section, in turn, surrounded at the top of the slanted section by a flat top section; and
    said positioning means is disc shaped and positioned in spaced relation above the top section of said reflector and in overlying relation with the slanted section of the reflector.

14. An apparatus according to claim 2 further comprising:
    a second ultraviolet light source positioned in said working chamber on the side of said portal opposite said first light source.

15. An apparatus according to claim 14 further comprising:
    shield means disposed in said working chamber between said second light source and said portal for shielding said second light source against contact with objects placed through said portal and into said working chamber, said shield being constructed of material which is transparent to ultraviolet light from said second light source.

16. An apparatus according to claim 14 further comprising:
    a third ultraviolet light source positioned in said second chamber between said reflector and said air inlet opening for irradiating air passing through said air inlet opening and into said second chamber and for irradiating the surfaces of all structure disposed within said second chamber.

17. The apparatus according to claim 16 further comprising a support disposed in the second chamber for supporting said third light source; and
    detachable means for removably connecting said support to the wall of said second chamber.

18. An apparatus according to claim 1 wherein:
    there are two portals positioned and sized to allow insertion of hands and lower arms into the working chamber.

19. An apparatus according to claim 18 further comprising:
    a collar extending externally of the working chamber and in surrounding relation to each of said portals, each of said collars being of low reflective material and opaque to said ultraviolet light.

20. An apparatus according to claim 1 wherein:

the working chamber includes an internal wall surface which is shaped and of a material which reflects the ultraviolet light from the source to provide irradiated ultraviolet light which is of uniform intensity throughout said working chamber.

21. An apparatus according to claim 1 wherein:

the working chamber is formed in three zones including an upper toroidal zone, a central cylindrical zone and a bottom toroidal zone, said bottom toroidal zone being truncated by the diffuser.

22. An apparatus according to claim 1, wherein:

the working chamber is divided into annular zones having different configurations to facilitate reflection of ultraviolet light throughout the working chamber, said zones including a first upper zone defining an upper portion of the working chamber and having a first toroidal configuration, a second central zone disposed below said first zone and defining a central segment of the working chamber and having a cylindrical configuration and a third bottom zone disposed below said second zone and defining a lower portion of the working chamber and having a second toroidal configuration.

23. An apparatus according to claim 22 wherein:

the first toroidal configuration has a center of rotation defined by a circle disposed between said upper zone and said central zone; and the second toroidal configuration has a center of rotation defined by a circle disposed between said central zone and said lower zone.

24. An apparatus according to claim 23 wherein:

the first and second toroidal configurations each have a radius of about ten inches and a center of rotation defined by a circle having a diameter of about three inches; and said cylindrical configuration has an axial length of between about three to five inches.

25. An apparatus according to claim 24 further comprising:

a reflector positioned on the other side of the ultraviolet light source from the diffuser.

26. An apparatus according to claim 1 wherein:

the wave length of the ultraviolet source weighted at 253.7 nm and at an energy level of approximately 3.0 joules/meter squared, is maintained throughout the working chamber.

27. An apparatus according to claim 1 further comprising:

means within said housing for maintaining air in the working chamber at a positive pressure in comparison to ambient air at the portal so as to prevent non-germicidally cleansed ambient air from entering the working chamber through the portal.

28. An apparatus according to claim 1, further comprising:

an ultraviolet opaque window at the top of the working chamber to allow visual inspection of the working chamber.

29. An apparatus according to claim 1, wherein:

said housing includes a lower housing member and an upper housing member removeably connected to said lower housing member in the area of said working chamber; and said ultraviolet light source and diffuser are positioned in said lower housing member.

30. A method of germicidally cleansing hands and lower arms comprising the steps of:

uniformly irradiating a working chamber with ultraviolet light;

inserting the hands and lower arms which are to be germicidally cleansed into said chamber for a period of time for germicidal cleansing thereof; and removing said hands and lower arms from said chamber.

31. A method according to claim 30 further comprising the step of:

irradiating said working chamber from a light source of said light located outside of said chamber.

32. A method according to claim 31, further comprising the step of:

rotating said hands and lower arms to assure uniform irradiation of all surfaces of said hands and lower arms.

33. A method according to claim 31 further comprising the steps of:

irradiating said working chamber from a light source of said light located in a second chamber which communicates with said working chamber;

diffusing said light as it passes along a path from said second chamber into said working chamber; and directing air from said second chamber past said light source and in the direction of the path of said light into said working chamber.

34. A method according to claim 33 further comprising the step of:

creating turbulent air flow patterns in the working chamber with the air flowing into said working chamber.

35. A method according to claim 34 further comprising the step of:

maintaining the ultraviolet light in said working chamber at a wave length weighted at 253.7 nm and at an energy level of approximatley 3.0 joules/meter squared.

* * * * *